(12) United States Patent
Filippi et al.

(10) Patent No.: US 8,158,074 B2
(45) Date of Patent: Apr. 17, 2012

(54) WALL SYSTEM FOR CATALYTIC BEDS OF SYNTHESIS REACTORS

(75) Inventors: Ermanno Filippi, Castagnola (CH); Enrico Rizzi, Casnate Con Bernate (IT); Mirco Tarozzo, Ligornetto (CH)

(73) Assignee: Ammonia Casale S.A. (CH)

( * ) Notice: Subject to any disclaimer, the term of this patent is extended or adjusted under 35 U.S.C. 154(b) by 244 days.

(21) Appl. No.: 12/162,446

(22) PCT Filed: Jan. 16, 2007

(86) PCT No.: PCT/EP2007/000315
§ 371 (c)(1),
(2), (4) Date: Sep. 22, 2008

(87) PCT Pub. No.: WO2007/093254
PCT Pub. Date: Aug. 23, 2007

(65) Prior Publication Data
US 2009/0047195 A1    Feb. 19, 2009

(30) Foreign Application Priority Data

Feb. 13, 2006    (EP) .................................. 06002825

(51) Int. Cl.
*B01J 8/02* (2006.01)
*B01J 8/04* (2006.01)
*B01J 8/44* (2006.01)

(52) U.S. Cl. ........ 422/218; 422/633; 422/636; 422/637; 422/648; 422/239; 422/311

(58) Field of Classification Search ................. 422/190, 422/192, 211, 218, 239, 311, 633, 636, 637, 422/648
See application file for complete search history.

(56) References Cited

U.S. PATENT DOCUMENTS

| | | |
|---|---|---|
| 4,849,206 A | 7/1989 | Zardi |
| 4,971,771 A | 11/1990 | Stahl |
| 5,827,485 A | 10/1998 | Libal et al. |
| 6,086,659 A | 7/2000 | Tentarelli |

FOREIGN PATENT DOCUMENTS

| | | |
|---|---|---|
| EP | 0365929 A2 | 5/1990 |
| EP | 0446592 A1 | 9/1991 |
| EP | 1145761 A1 | 10/2001 |

*Primary Examiner* — Walter D Griffin
*Assistant Examiner* — Lessanework Seifu
(74) *Attorney, Agent, or Firm* — Akerman Senterfitt

(57) ABSTRACT

Described here is a system (8; 9; 50) of walls for catalytic beds of reactors (1) for the heterogeneous synthesis of chemical compounds characterized in that it comprises a wall (14) of predetermined thickness in direct contact with a catalytic bed (7) for containing it, said wall having a plurality of portions (17) permeable to gases and a plurality of portions (19; 54; 55) impermeable to gases, said portions (17) permeable to gases each being equipped with a plurality of slits (18; 52, 53; 60; 70) of a size such as to allow the free passage of the synthesis gases through them but not the passage of the catalyst.

9 Claims, 6 Drawing Sheets

US 8,158,074 B2

WALL SYSTEM FOR CATALYTIC BEDS OF SYNTHESIS REACTORS

FIELD OF APPLICATION

The present invention, in its more general aspect, concerns the field of heterogeneous catalytic synthesis of chemical compounds through reactors equipped with fixed catalytic beds crossed by a gaseous flow of synthesis gas particularly with radial, axial-radial or axial motion. In particular the present invention concerns a system of walls for catalytic beds of synthesis reactors quoted above and a reactor comprising said system of walls.

PRIOR ART

As it is well known, in reactors with fixed catalytic beds used for heterogeneous catalytic synthesis of chemical compounds, such as for example ammonia and methanol, system of walls are envisaged in particular for the distribution of the synthesis gases inside said catalytic beds. Such systems of walls are designed and built so as to satisfy certain functional requirements necessary for the synthesis reactor to operate correctly, including:
- permeability to the gaseous flow of synthesis gases so as to allow a suitable load loss such as to allow an optimal distribution thereof on the entire catalytic bed,
- containment and mechanical support of the catalytic mass so as to balance the thrusts resulting from the mass of the catalyst (it own weight and thrusts due to the differences in dilation between catalyst and containment walls) and the thrusts of the gases that cross the catalytic bed.

More specifically, in order to satisfy the aforementioned requirements, it is known to use systems of walls for catalytic beds consisting of a plurality of walls each of which carries out one or more of the aforementioned functions.

An example of a system of walls used for the distribution of synthesis gas in catalytic beds is described in patent application FR 2615407. More specifically, in this document, is disclosed a distribution system of synthesis gas in a catalytic bed of a reactor consisting of a plurality of tubular modules (known as scallops) with substantially arch-shaped profile brought close together to form a gas distribution wall. Each tubular module is closed at its bottom end, open at the opposite end for the entry of the gases and has a wall that is impermeable to gases, through which it is brought close to the shell of the reactor or, in the case in which there is a cartridge for the catalyst, to the inner wall of the cartridge, and a grid that is permeable to the gases. The grid consists of a series of parallel longitudinal metal rods (i.e. parallel to the axis of the reactor) in spaced apart relationship and welded to a series of transversal rods also in a suitable spaced apart relationship. The longitudinal rods are also welded at respective ends to suitable ring-arch-shaped supports. The grid of each tubular module is in direct contact with the catalyst and essentially carries out the functions of containment and support of the catalyst at the same time allowing the free passage of the gases into the catalyst but not allowing the catalyst to pass through it. Inside each tubular module a perforated wall is also envisaged fixed to the longitudinal edges of the grid so as to create an interspace with it for a load loss of the entering gases useful for allowing a their optimal distribution inside the catalytic bed.

The aforementioned system of walls with tubular modules does, however, have various drawbacks including a certain difficulty in construction and assembly due in particular to the fact that it is necessary to carry out a series of welds to put the rods of the grid in place.

Moreover, in the case of a reactor for ammonia synthesis, it is known that the inner components of the reactor and in particular the walls of the gas distribution system in the catalytic beds, are subjected to surface nitriding effects in normal operating conditions of the reactor that result in a progressive reduction of the mechanical strength of said components. In this circumstance, in the case of use of the aforementioned systems of walls with tubular modules it is necessary to disadvantageously use materials that are highly resistant to nitriding and notoriously much expensive, such as for example the special steels Inconel® (iron-nickel alloys), for the low-thickness elements, like the rods of the grid, in order to keep a satisfactory mechanical strength during the operation of the reactor.

On the other hand, it should be noticed that the thicker elements of the aforementioned wall systems can be formed with conventional materials that are therefore less expensive (for example stainless steel) but this involves that it is necessary to carry out heterogeneous welds (i.e. between different materials) which, in turn, are subjected to the formation of cracks or breaks as a result of the thermal stress due to the differences in thermal expansion coefficients of the materials used. The technical problem at the basis of the present invention is that of providing a system of walls for catalytic beds of synthesis reactors, in particular for the distribution of synthesis gas in said catalytic beds, which overcomes the aforementioned drawbacks and in particular a system of walls for catalytic beds that is easy and cost-effective to make and that has adequate characteristics of mechanical strength and resistance to nitriding effects in normal operating conditions of the synthesis reactor in which it is used.

SUMMARY OF THE INVENTION

This problem is solved by a system of walls for catalytic beds of reactors for the heterogeneous synthesis of chemical compounds characterised in that it comprises a wall of predetermined thickness in direct contact with a catalytic bed for containing it, said wall having a plurality of portions permeable to gases and a plurality of portions impermeable to gases, said portions permeable to gases each being equipped with a plurality of slits of a size such as to allow the free passage of the synthesis gases through them but not allow the passage of the catalyst. Preferably, the aforementioned containment wall has a thickness within the range from 1 to 10 mm, preferably from 3 to 6 mm. Preferably, the aforementioned containment wall also constitutes a mechanical support for said catalytic bed through said portions impermeable to gases. Preferably the aforementioned containment wall consists of a plurality of modules fixed together in which each module comprises said portions permeable to gases and/or said portions impermeable to gases.

The slits can be of any shape, rectilinear or curvilinear and can be arranged in any way, for example they can have a longitudinal or transversal extension with reference to the axis of the reactor in any combination of slits—rectilinear, curvilinear or both.

According to a preferred embodiment of the invention, the system of walls according to the invention further comprises a distribution wall equipped with gas-permeable portions arranged in spaced relationship with said containment wall so as to create an interspace with it. Preferably, the gas-permeable portions of the distribution wall consist of a plurality of holes made in said wall. Preferably, said gas-permeable portions of the distribution wall are arranged side-by-side towards the gas-impermeable portions of the containment wall so as to avoid the direct impact of the synthesis gases that cross the gas-permeable portions with the catalyst. Differently, in the case of the systems of walls of the aforementioned prior art, it is not possible to protect the catalyst from the direct impact of the synthesis gases coming out from the distribution wall.

The aforementioned distribution wall is per se conventional and can be equipped with spacing means, also of the conventional type, to stably maintain the containment wall of the catalyst and the distribution wall in the desired spaced relationship also in conditions of great mechanical or thermal stress to which said walls can be subjected inside the reactor in its normal operating conditions.

The main advantage of the system of walls according to the invention lies in the simplicity of making it since the gas-permeable portions, in other words the aforementioned slits, are formed directly in the thickness of the modules of the containment wall of the catalyst therefore without having to carry out a plurality of welds as required to make the grids in the system of walls of the aforementioned prior art.

Moreover, the presence of portions impermeable to gases gives the aforementioned containment wall adequate mechanical strength that makes it in general suitable to withstand the mechanical and thermal stresses in normal operating conditions of the reactor. Advantageously, such mechanical strength can also be suitable for the specific requirements of use in the reactor for which it is intended by suitably adjusting the thickness of the containment wall of the catalyst so as to satisfy such requirements.

For example, the thickness of the containment wall can be such that such a wall is able to also act as a support of the catalyst through its portions impermeable to the gases. Alternatively, the catalyst support function can be partially or completely carried out by the distribution wall by suitably adjusting the thickness thereof so as to have a suitable mechanical strength.

It should also be noticed that in the system of walls according to the invention it is not necessary to use expensive materials for both the containment wall and the distribution wall, thus resulting in a substantial saving in production costs.

For example, in the case of use of the system of walls according to the invention in a reactor for ammonia synthesis, it is possible to use a relatively inexpensive material, such as for example stainless steel, to make both the containment and distribution walls, obtaining suitable mechanical strength and resistance to nitriding effects. In particular the negative effects on mechanical strength deriving from surface nitriding can be compensated by suitably adjusting the thickness of said walls or, in the case of the containment wall of the catalyst, the distribution and the number of portions permeable to gases and of portions impermeable to gases.

Differently, in the case of wall systems of the prior art it is necessary to use very expensive materials that are highly resistant to nitriding such as for example the special steels Inconel® (iron-nickel alloys), for the low-thickness elements (for example the welded rods of the grid), in order to keep a satisfactory mechanical strength during the operation of the reactor.

It should also be noticed that, advantageously, the slits of the portions permeable to gases can be arranged according to a predetermined order and number along the entire containment wall of the catalyst to satisfy contingent and specific requirements, without substantially compromising in this way the mechanical strength of said wall.

The present invention also concerns a reactor for the heterogeneous synthesis of chemical compounds comprising a shell closed at the opposite ends by respective bottoms, an opening for the inlet of synthesis gases, an opening for the outlet of the reaction products, at least one catalytic bed and at least one system of walls for said at least one catalytic bed as described above.

The reactor according to the invention can be of the type with crossing of the gases in the catalytic bed or in the catalytic beds with radial, axial-radial or axial motion.

In particular, in the case of reactors with crossing of said at least one catalytic bed by the gases with radial or axial-radial motion, the system of walls according to the invention can be arranged on an inlet side of the gases in said at least one catalytic bed and/or on an outlet side of the gases from said at least one catalytic bed with the respective containment walls in contact with the catalyst.

Advantageously, with the system of walls according to the invention, an optimal distribution of the synthesis gases is obtained, on the gas inlet side, inside the respective catalytic bed thanks to the fact that the gases crossing the holes of the distribution wall undergo a load loss in the interspace between the distribution wall and the containment wall, which allows the inlet speed of said gases into the catalytic bed to be reduced. However, it should be noticed that other embodiments of the reactor are also possible in which the distribution wall of the system of walls according to the invention is left out on the gas inlet side in the respective catalytic bed or on the gas outlet side from the respective catalytic bed.

In the reactor according to the invention, the systems of walls of the catalytic beds are supported in a conventional manner inside the reactor. In the case a cartridge for containing said catalytic beds permeable to gases is envisaged inside the reactor, the systems of walls for gas inlet according to the invention are arranged at the inner wall of said cartridge with the respective containment walls in contact with the catalyst of the respective catalytic beds.

In the case of reactors with crossing of said at least one catalytic bed by the gases with axial motion, the system of walls according to the invention can be applied onto the upper gas-inlet bottom and/or onto the lower gas-outlet bottom of the respective catalytic bed.

Advantageously, on the upper gas-inlet bottom, the system of walls according to the invention can be used in place of the usual protective grids of the catalyst at the same time obtaining an optimal distribution of the synthesis gases in the catalytic bed.

Further characteristics and advantages of the present invention shall also become clear from the following description of some preferred example embodiments thereof, given for representative and not limiting purposes, with reference to the attached figures.

DETAILED DESCRIPTION

Figure 1:
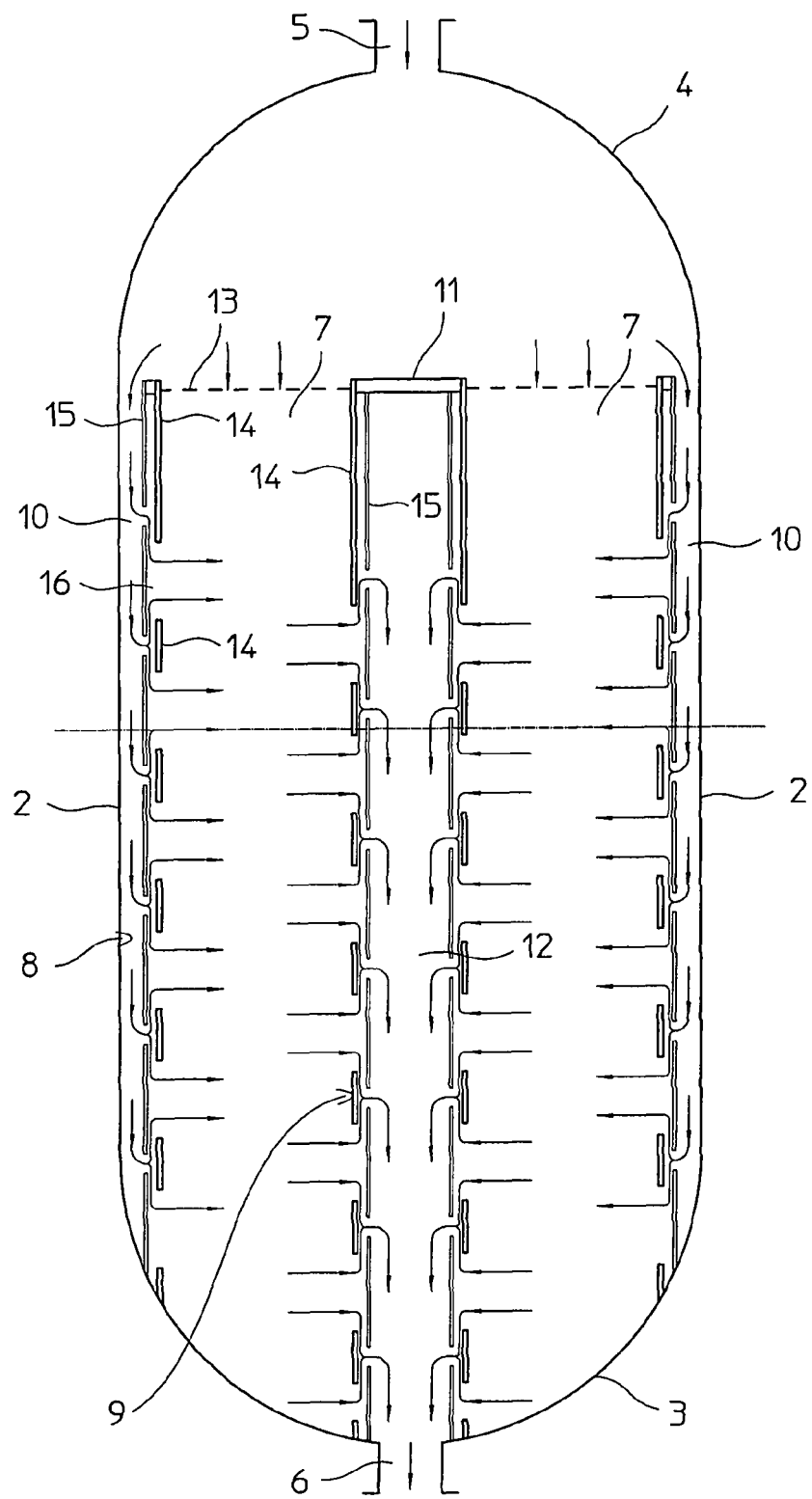
FIG. 1 schematically shows a longitudinal section view of a reactor for the heterogeneous synthesis of chemical compounds incorporating, according to the invention, a system of walls for the inlet of gas into a catalytic bed and a gas outlet system from said catalytic bed, FIG. 2 schematically shows a cross section view of the reactor of FIG. 1, FIG. 3 schematically shows a perspective view of a section of the system of walls for the inlet of gas and of the system of walls for the outlet of gas of the reactor of FIG. 1, FIG. 4 schematically shows a perspective view of a section of only the system of walls for the outlet of gas of the reactor of FIG. 1, FIG. 5 schematically shows a perspective view of a section of a system of walls for the outlet of gas from a catalytic bed according to a another embodiment of the invention, and FIG. 6 schematically shows a detail of a system of walls according to a further embodiment of the present invention.

With reference to the aforementioned figures, a reactor for the heterogeneous synthesis of chemical compounds is globally indicated with 1.

The reactor 1 comprises a substantially cylindrical shell 2 closed at the opposite ends by respective upper bottom 3 and lower bottom 4. The reactor 1 is also provided on the upper bottom 4 with an opening 5 for the inlet of a gaseous flow of reactant gases and on the bottom 3 with an opening 6 for the outlet of a gaseous flow comprising the reaction products.

Inside the shell 2 an annular catalytic bed 7 of the type with axial-radial crossing is formed, which is laterally delimited by respective systems of walls according to the invention, globally indicated with 8 and 9 respectively for the inlet and for the outlet of the gases from the catalytic bed 7. The relevant characteristics of the systems of walls 8 and 9 according to the invention shall be made clearer in the remainder of the present description.

The catalytic bed 7 is not closed on top to allow it to be crossed axially by a portion of the flow of reactant gases and it is also delimited at the bottom by the lower bottom 3 of the reactor 1.

Figure 2:
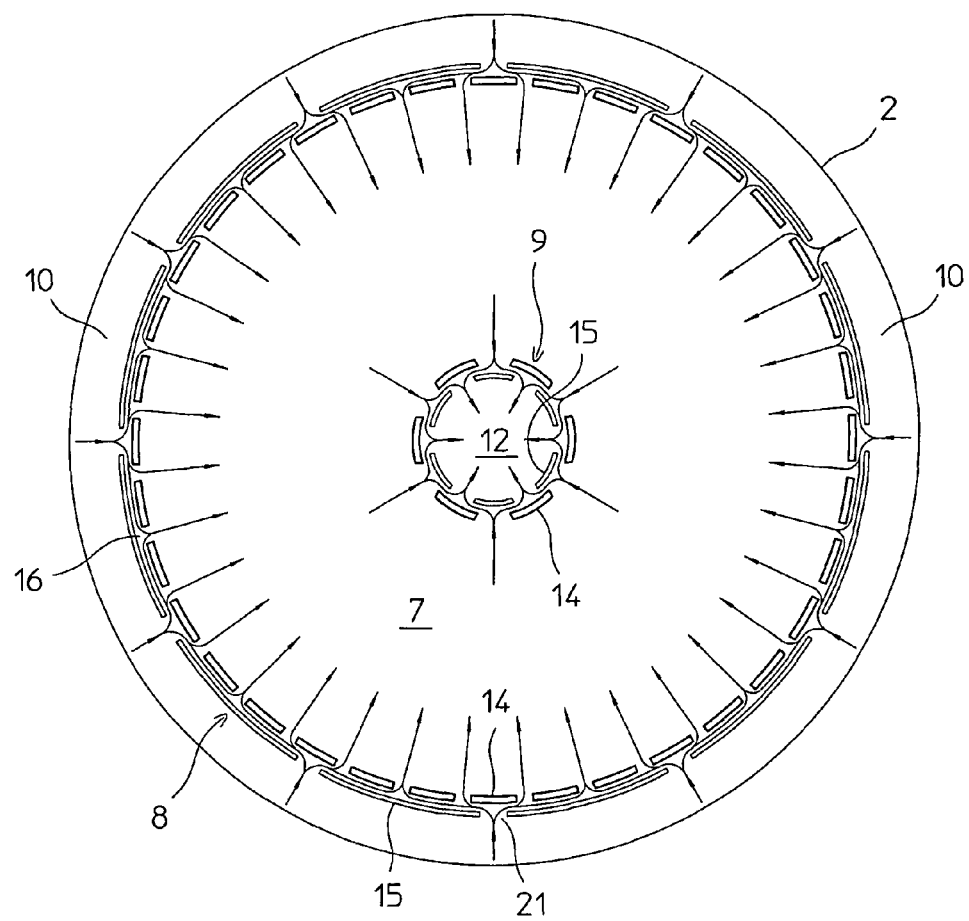

In the reactor 1 shown in FIGS. 1 and 2, the system of walls 8 for the inlet of gas is arranged close to the shell 2 whereas the system of walls 9 for the outlet of gas is arranged centrally to the reactor 1. An annular interspace 10 is therefore defined between the shell 2 and the system of walls 8 for the inlet of gas to allow the catalytic bed 6 to be crossed radially by a portion of the gaseous flow of reactant gases.

The system of walls 9, instead, is closed on top by a cover 11 not permeable to the gases, of the known type. A chamber 12 is also envisaged, which extends coaxially to the catalytic bed 7, between the system of walls 9 and the cover 11, for sending the reaction products coming out from such a catalytic bed to the opening 6 for the outlet of them from the reactor 1.

The broken line 13 represented in FIG. 1 at the top end of the system of walls 8 for the inlet of gas, delimits the maximum level that can be reached by the catalyst inside the catalytic bed 7, and defines, together with the systems of walls 8 and 9 and with the lower bottom 3, the reaction volume available in the reactor 1.

In FIGS. 1 and 2 the arrows indicate the various paths followed by the gases inside the reactor and in particular through the catalytic bed 7. In accordance with the present invention, the system of walls 8 for the inlet of gas, as the system of walls 9 for the outlet of gas, consists of two substantially cylindrical walls 14, 15, coaxial and spaced apart so as to form an annular interspace 16 between them.

Figure 3:
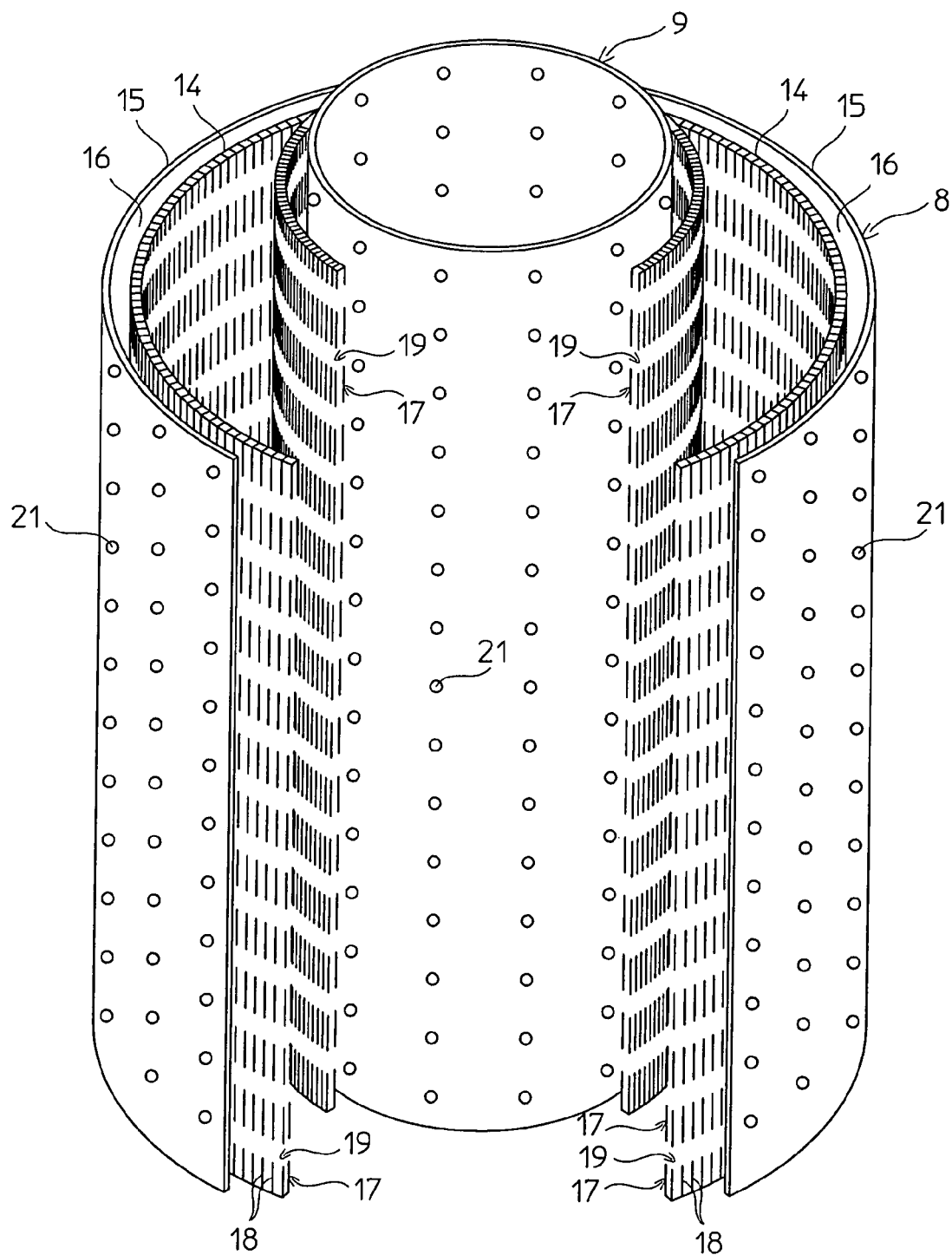
Figure 4:
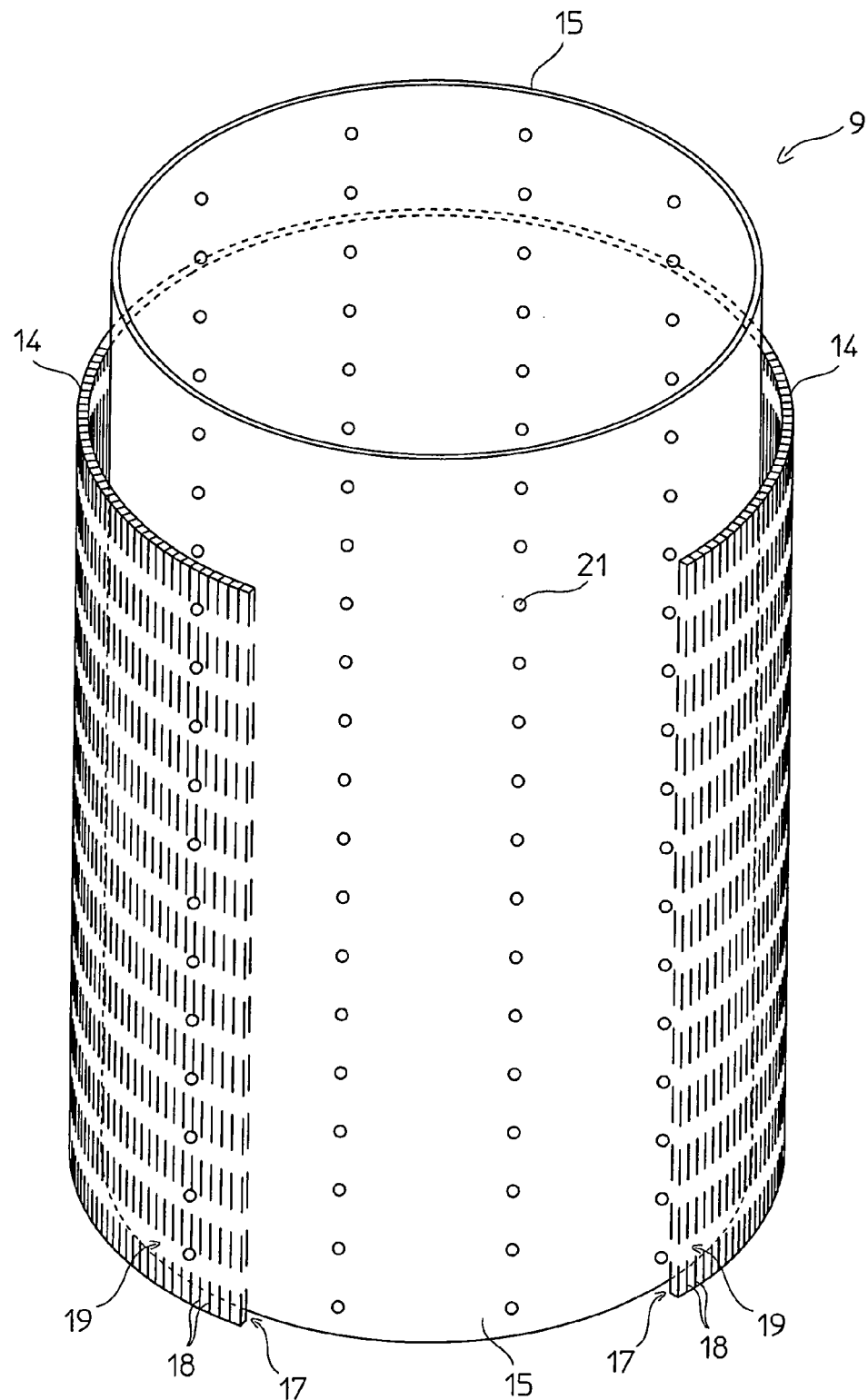

More specifically (FIGS. 3 and 4), the wall 14 of each of the systems of walls 8 and 9 is in direct contact with the catalyst of the catalytic bed 7 for the lateral containment thereof and has a plurality of areas or portions 17 in the form of circumferential bands equipped with a plurality of axial slits 18 (i.e. extending parallel to the longitudinal axis of the shell 2) alternating with "full" areas or portions 19, in other words without slits, also in the form of circumferential bands. The slits 18 are of a size such as to allow the free passage through them of the gases but not of the catalyst of the catalytic bed 7. Regarding this, the slits 18 can have a width of between 0.3 and 2 mm, preferably between 0.5 and 0.8 mm. The slits 18 can be formed through notches in the material of which the containment wall 14 consists through per se conventional processes for making notches in metal plate. Preferred processes for making the notches 18 comprise processes of shearing with lasers or with water that, advantageously, allow notches to be made in substantially all types of metal materials used to make containment walls 14 without problems of wear of the tools used to make said notches as occurs in other techniques.

The containment wall 14 is advantageously formed with a suitable thickness and material such as to have good mechanical strength during the operation of the reactor also under the effect of nitriding or other corrosion effects. As an example, in the case of a reactor for ammonia synthesis, the containment wall 14 can be formed with a thickness of between 1 and 10 mm, preferably between 3 and 6 mm and the material of said wall can be any material having ordinary resistance to nitriding such as for example stainless steel. In this regard, it should be noticed that a wall made in this way, although it is subjected to surface nitriding effects typical of ammonia synthesis, effects that would tend to make it weak over time, it maintains adequate mechanical strength during normal conditions of use of the reactor 1. It should also be noticed that the containment wall 14 can be formed with a suitable thickness so as to act other than for containment also as a mechanical support for the catalytic bed 7 through the respective "full" portions 19, i.e. without slits 8.

The distribution wall 15 of each of the systems of walls 8 and 9, instead, consists of a plate of suitable thickness equipped with a plurality of holes 21 arranged, in the example shown here, in parallel axial groups in predetermined spaced apart relationship. More specifically, the holes 21 preferably face towards the areas or portions impermeable to gases of the containment wall 14 so as to avoid the direct impact of the gases with the catalyst. In the example shown in the figures, such areas or portions impermeable to gases consist of full areas or portions 19 between the slits 18 of the wall 14.

As for the system of walls 8 for the inlet of gas, the function of the wall 15 is essentially to promote the uniform distribution of gases entering the catalytic bed 7 as shell be described more clearly hereafter. The wall 15 is made from a conventional material, for example stainless steel, and obtained through conventional processes with a suitable thickness according to requirements. Preferably, the distribution wall 15 is obtained with a suitable thickness to act as a mechanical support for the catalytic bed 7. The distribution wall 15 can also be equipped with spacers (not shown) to stably maintain the spaced relationship with the containment wall 14 under the effect of mechanical or thermal stresses during the operation of the reactor 1.

Preferably, each of the aforementioned walls 14 and 15 of a system of walls 8 or 9 is formed from longitudinal modules (not shown) of a suitable size to pass through a "manhole" (also not shown) of the reactor 1, said modules then being fixed together (for example welded or bolted) to form the corresponding walls.

Figure 5:
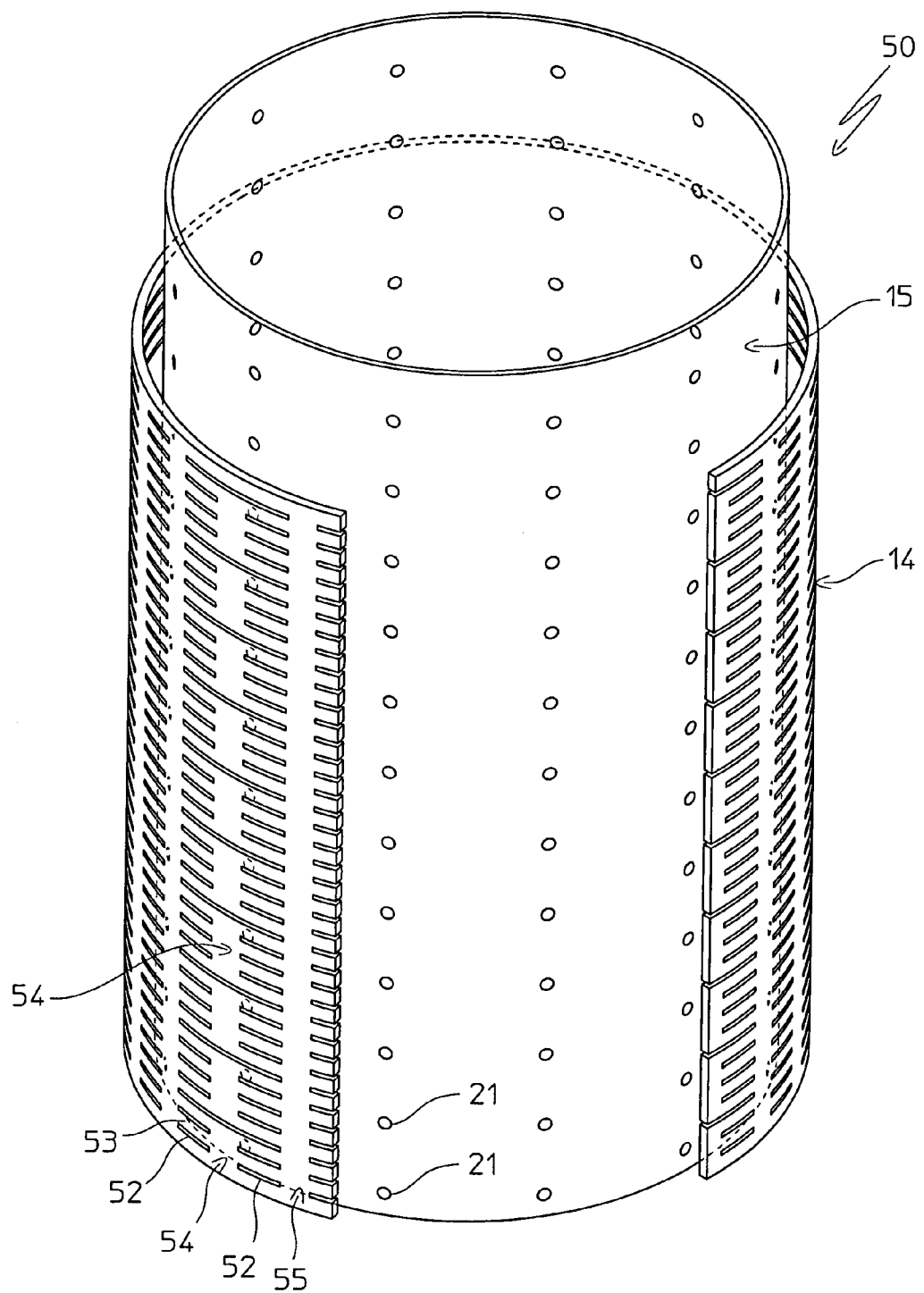

As mentioned previously, the reactor 1 comprises a system of walls 8 for the inlet of the gases into the catalytic bed 7 and a system of walls 9 for the outlet of the gases from said catalytic bed, the walls 14 and 15 of which have been described up to now with regard to their structure. It should now be noticed that, in the case of the system of walls 8 for the inlet of gas, the distribution wall 15 is arranged outside (going from the axis of the reactor towards the shell) with respect to the containment wall 14 of said system 8 of walls and forms with the shell 2 the interspace 10. In this way, the gases that cross the annular interspace 10 pass through the holes 21 of the distribution wall 15 and expand in the interspace 16 between the walls 14 and 15, thus obtaining a load loss that allows the same gases to be distributed uniformly in the catalytic bed 7 after having crossed the slits 18 of the wall 14 in contact with the catalyst. Vice-versa, in the system of walls 9 for the outlet of gas, the wall 15 is more inner than the containment wall 14. Therefore, the gases that radially cross said catalytic bed 7 come out from it crossing the slits 18 of the wall 14 of the system 9 of walls and passing through the interspace 16, the holes 21 of the wall 15. Then they are collected in the chamber 12 and from here conveyed towards the outlet opening 6 of the reactor 1. FIG. 5 shows a system of walls for catalytic beds of synthesis reactors according to another embodiment of the invention, said system being globally indicated with 50. The elements of the system of walls 50 that are structurally or functionally equivalent to corresponding elements of the systems of walls 8 and 9 described previously shall be attributed the same reference numerals.

The system of walls 50 shown in FIG. 5 comprises a containment wall 14 and a substantially cylindrical wall 15, coaxial and spaced apart so as to form an annular interspace 16 between them. In the containment wall 14 it is possible to distinguish a plurality of arc-shaped slits 52 having a shorter length, a plurality of arc-shaped slits 53 having a longer length and portions 54 and 55 impermeable to gases.

The system of walls 50 is suitable in particular for being applied onto the outlet side of a catalytic bed crossed by the gases with radial or axial-radial motion since the wall 15 is arranged inside the containment wall 14. Of course, by inverting the arrangement of the walls 14 and 15 with respect to each other, the system of walls 50 described above can also be applied to the gas inlet side into the catalytic bed.

Figure 6:
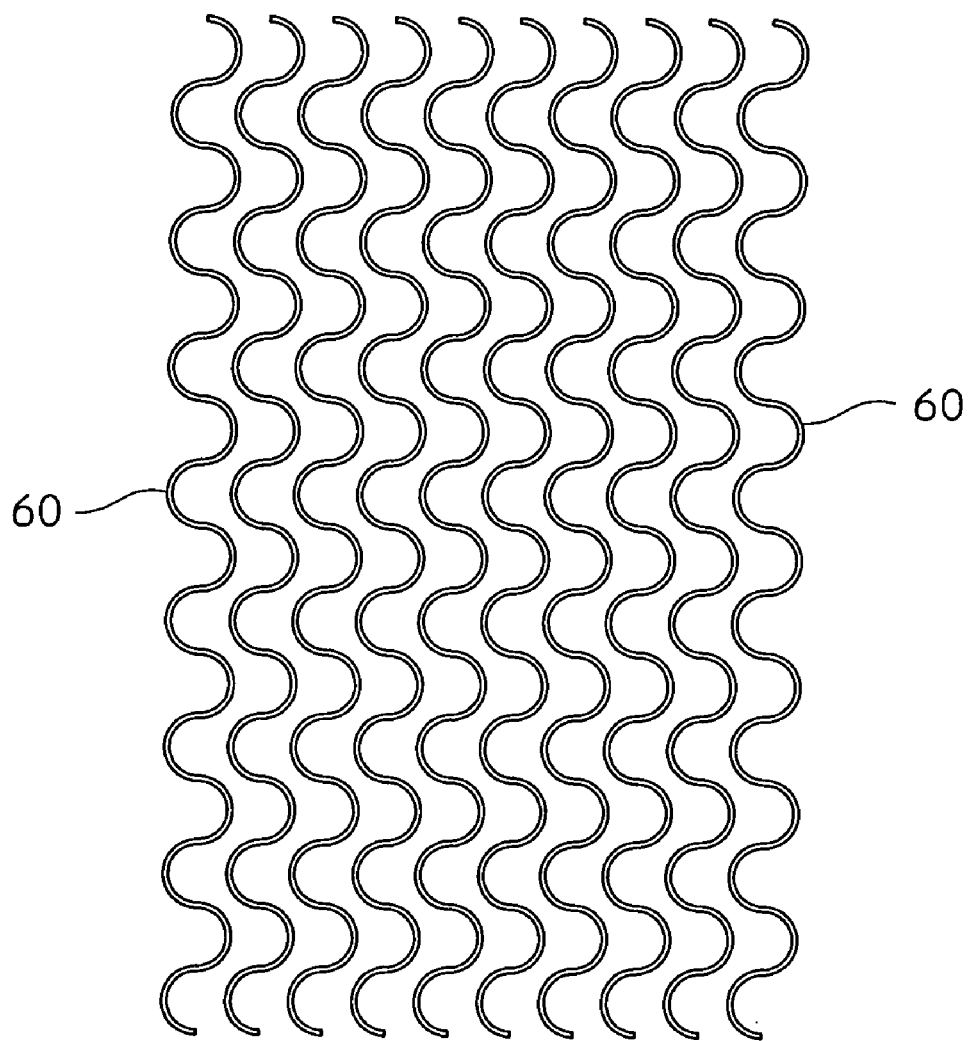

FIG. 6 schematically shows an alternative form and arrangement of slits on the containment walls 14 of the wall systems according to the invention. In particular, FIG. 6 shows a plurality of slits 60 arranged axially and each being substantially coil-shaped. Such a coil-shaped arrangement of slits advantageously offers a larger surface available for the crossing of gases at the same mechanical strength of said containment wall 14.

Of course, a man skilled in the art can bring numerous modifications and variants to the system of walls and to the reactor described above, all of which are covered by the scope of protection of the following claims.

The invention claimed is:

1. A reactor for the heterogeneous synthesis of chemical compounds, comprising:
    a shell closed at the opposite ends by respective bottoms;
    an opening for the inlet of synthesis gas;
    an opening for the outlet of the reaction products; and
    at least one catalytic bed having a gas inlet side or bottom and a gas outlet side or bottom, said at least one catalytic bed being delimited at least one of said gas inlet side/bottom or gas outlet side/bottom by at least one system of walls for said at least one catalytic bed,
    wherein said at least one system of walls comprises a containment wall in direct contact with said catalytic bed for containing it,
    said wall having a plurality of portions permeable to gases and a plurality of portions impermeable to gases,
    said portions permeable to gases each being equipped with a plurality of slits of a size such as to allow the free passage of the synthesis gases through them but not the passage of the catalyst,
    said portions impermeable to gases constituting a mechanical support for said catalytic bed, and
    a distribution wall equipped with gas-permeable portions arranged in spaced relationship with said containment wall so as to create an interspace with it.

2. The reactor according to claim 1, wherein said containment wall of said catalytic bed has a thickness within the range from 1 to 10 mm.

3. The reactor according to claim 1, wherein said containment wall consists of a plurality of modules in which each module comprises said portions permeable to gases and/or said portions impermeable to gases.

4. The reactor according to claim 1, wherein said gas-permeable portions of the distribution wall consist of a plurality of holes made in said wall and facing towards said portions impermeable to gases of the containment wall of said catalytic bed.

5. The reactor according to claim 1, wherein said slits are coil-shaped.

6. The reactor according to claim 1, wherein said slits have a width of between 0.3 and 2 mm.

7. The reactor according to claim 1, wherein said synthesis gases cross said at least one catalytic bed with radial or axial-radial motion and in that it comprises a system of walls on a gas inlet side of said at least one catalytic bed and a system of walls on a gas outlet side of said at least one catalytic bed.

8. The reactor according to claim 2, wherein said containment wall of said catalytic bed has a thickness within the range from 3 to 6 mm.

9. The reactor according to claim 6, wherein said slits have a width of between 0.5 and 0.8 mm.

* * * * *